US010617312B2

(12) United States Patent
Carmi et al.

(10) Patent No.: US 10,617,312 B2
(45) Date of Patent: Apr. 14, 2020

(54) PERFUSION IMAGING

(71) Applicant: KONINKLIJKE PHILIPS N.V., Eindhoven (NL)

(72) Inventors: Raz Carmi, Haifa (IL); Galit Sarit Kafri, Newton, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1359 days.

(21) Appl. No.: 14/394,110

(22) PCT Filed: Apr. 10, 2013

(86) PCT No.: PCT/IB2013/052848
§ 371 (c)(1),
(2) Date: Oct. 13, 2014

(87) PCT Pub. No.: WO2013/156901
PCT Pub. Date: Oct. 24, 2013

(65) Prior Publication Data
US 2015/0080707 A1 Mar. 19, 2015

Related U.S. Application Data

(60) Provisional application No. 61/625,143, filed on Apr. 17, 2012.

(51) Int. Cl.
*A61B 5/0275* (2006.01)
*A61B 5/055* (2006.01)
(Continued)

(52) U.S. Cl.
CPC .......... *A61B 5/0275* (2013.01); *A61B 5/0555* (2013.01); *A61B 6/032* (2013.01);
(Continued)

(58) Field of Classification Search
CPC ..... A61B 5/0037; A61B 5/0275; A61B 5/055; A61B 5/0555; A61B 6/032; A61B 6/507; A61B 6/481; A61B 6/504; A61B 8/543
See application file for complete search history.

(56) References Cited

U.S. PATENT DOCUMENTS 6,015,384 A * 1/2000 Ramamurthy ........... A61B 8/06
600/440
6,645,147 B1 * 11/2003 Jackson ................... A61B 8/06
600/458

(Continued)

FOREIGN PATENT DOCUMENTS

WO 2008132386 A2 11/2008

OTHER PUBLICATIONS

Andersen et al: "Perfusion Quantification Using Gaussian Process Deconvolution"; Magnetic Resonance in Medicine, 48:351-361.
(Continued)

Primary Examiner — Baisakhi Roy
(74) Attorney, Agent, or Firm — Larry Liberchuk

(57) ABSTRACT

A method includes obtaining contrast enhanced perfusion imaging data of at least two vessel regions, one downstream from the other, and at least one tissue of interest, which receives blood from the circulatory system, of a scanned subject. The method further includes determining a blood flow time difference between contrast material peaks of the at least two vessel regions based on the image data. The method further includes determining an absolute perfusion of the tissue of interest based on the image data. The method further includes computing a standardized perfusion value based on the absolute perfusion and the time difference. The method further includes displaying the standardized perfusion value.

21 Claims, 9 Drawing Sheets

(51) Int. Cl.
*G06T 5/00* (2006.01)
*A61B 8/08* (2006.01)
*A61B 8/06* (2006.01)
*A61B 6/03* (2006.01)
*A61B 6/00* (2006.01)
*G01R 33/563* (2006.01)
*A61B 5/00* (2006.01)

(52) U.S. Cl.
CPC .............. *A61B 6/037* (2013.01); *A61B 6/481* (2013.01); *A61B 6/486* (2013.01); *A61B 6/507* (2013.01); *A61B 6/5217* (2013.01); *A61B 8/06* (2013.01); *A61B 8/481* (2013.01); *G01R 33/56366* (2013.01); *G06T 5/00* (2013.01); *A61B 5/0037* (2013.01); *A61B 5/055* (2013.01); *A61B 8/5223* (2013.01); *G06T 2207/30101* (2013.01)

(56) References Cited

U.S. PATENT DOCUMENTS

| | | |
|---|---|---|
| 7,627,360 B2 | 12/2009 | Kimura |
| 8,099,149 B2 | 1/2012 | Carroll et al. |
| 8,908,939 B2 | 12/2014 | Bredno et al. |
| 2004/0077941 A1* | 4/2004 | Reddy .................... A61B 6/032 600/428 |
| 2005/0283070 A1* | 12/2005 | Imielinska ............. A61B 6/032 600/425 |
| 2007/0269000 A1* | 11/2007 | Partain ................... A61B 6/032 378/37 |
| 2008/0319302 A1* | 12/2008 | Meyer .................. A61B 5/0263 600/410 |
| 2011/0213244 A1 | 9/2011 | Frinking et al. |
| 2011/0245687 A1* | 10/2011 | Rensen ................ A61B 5/0059 600/477 |
| 2012/0136243 A1* | 5/2012 | Boese .................. A61B 5/0275 600/425 |
| 2012/0141005 A1* | 6/2012 | Djeridane .......... A61B 5/02028 382/131 |
| 2012/0262562 A1* | 10/2012 | Fukutake ............... G02B 21/14 348/79 |

OTHER PUBLICATIONS

Griffiths: "Dynamic Contrast-Enhanced CT in the Investigation of Tumour Angiogenesis and Haemodynamics"; PHD Theses, Feb. 2007, Queensland University of Technology, 233 Pages.

Miles et al: "Standardized Perfusion Value: Universal CT Contrast Enhancement Scale That Correlates With FDG PET in Lung Nodules"; Radiology 2001, 220, pp. 548-553.

* cited by examiner

PERFUSION IMAGING

CROSS-REFERENCE TO PRIOR APPLICATIONS

This application is the U.S. National Phase application under 35 U.S.C. § 371 of International Application No. PCT/IB2013/052848, filed on Apr. 10, 2013, which claims the benefit of U.S. Provisional Patent Application No. 61/625,143, filed on Apr. 17, 2012. These applications are hereby incorporated by reference herein.

The following generally relates to perfusion imaging and is described with particular application to computed tomography (CT); however, the following is also amenable to other imaging modalities including magnetic resonance imaging (MRI), positron emission tomography (PET), single photon emission computed tomography (SPECT), ultrasound (US) and/or other imaging modalities.

A CT scanner includes an x-ray tube supported by a rotating frame. The rotating frame and hence the x-ray tube rotate around an examination region, and the x-ray tube emits radiation that traverses the examination region and a portion of a subject and/or object disposed therein. A radiation sensitive detector is located opposite the x-ray tube, across the examination region, and detects radiation that traverses the examination region and the subject and/or object. The radiation sensitive detector generates projection data indicative of the detected radiation. A reconstructor reconstructs the projection data and generates volumetric image data indicative of the subject and/or object. An image processor can be used to process the volumetric image data and generate one or more images indicative of the subject and/or object.

CT perfusion imaging provides functional information through imaging characteristics related to the blood flow in organs and tissues using a contrast material such as iodine contrast agent. A typical perfusion study requires repeated imaging of the volume of interest for a number of different time points, for example, 3-30 repeated scans with a few seconds difference between successive scans (e.g. 1 to 10 sec per time frame). In common perfusion techniques, a bolus of a contrast agent is administered into the patient's vascular system and images from the region of interest are collected for a period covering the transit of the contrast agent bolus through the tissue in the region of interest. The local concentration changes of the contrast agent (as can be inferred from image data) over time are used for analyzing physiological parameters.

Perfusion is particularly useful for studying patients with brain, heart or liver damage, e.g. as a result of stroke, tumors, infarct, etc. and general functionality of additional organs such as lungs and kidneys. In recent years it was shown that antiangiogenic agents may not significantly reduce tumor volume, especially soon after initiation of therapy, so conventional assessments of the tumor-size change may be insensitive to or provide markedly delayed indications of treatment response. Perfusion imaging of the microcirculation provides additional in vivo information and has a practical potential to be an important tool for assessing many types of cancer and tumors. In clinical practice, it is common for the perfusion image series to be inspected qualitatively or to be assessed quantitatively with special analysis algorithms.

For a quantitative absolute value, it is common to normalize the parameters derived from the tissue time attenuation curve (TAC) by parameters derived from the aorta TAC, or from another relevant artery which leads blood to the tissue. This absolute perfusion value (in units of 1/time or 1/time/density) is useful for assessing the physiology of the examined tissue, but it may be affected from other factors as well such as cardiac output and total body blood volume which may lead to errors and inaccuracies in the clinical diagnosis. For example, perfusion within a tissue with a particular micro-vessel density can also be increased by simply raising the cardiac output. In large patients, a correction for the total patient blood volume is also required because a higher cardiac output would be distributed throughout a greater blood volume with no change in delivery of blood to a given tissue. The literature has suggested using a standardized perfusion value (SPV) as a metric to quantify perfusion.

One formulation is: $SPV=(P \times W)/(C/A)$ where P is the absolute perfusion value, W is the patient weight, C is the total contrast material dose multiplied by the correct conversion to Hounsfield units (HU), and A is the area under the arterial time attenuation curve corrected for recirculation. The ratio C/A is assumed to be approximately proportional to the patient cardiac output. Unfortunately, this approach has limitations and inaccuracies. For example, the external information of patient weight, injected dose, and conversion function to HU may not be available or reliable. Next, the ratio W/(C/A) is not really proportional (or equal) to the total body perfusion as the patient weight is not a suitable factor since bones and fat regions are very weekly related to perfusion processes. In addition, many diseases and physical conditions may change the body perfusion. Some variations in the calculation may be due to inaccurate contrast material quantification, e.g., different iodine HU can be obtained in different x-ray tube energies due to varying beam hardening.

In view of at least the above, there is an unresolved need for other approaches for determining an SPV, for example, an SPV that is more accurate and reliable than the formulation discussed above and/or other formulations.

Aspects described herein address the above-referenced problems and others.

In one aspect, a method includes obtaining contrast enhanced perfusion imaging data of at least two vessel regions, one downstream from the other (with respect to the contrast agent bolus flow), and at least one tissue of interest, which receives blood from the circulatory system, of a scanned subject. The method further includes determining a blood flow time difference between contrast material peaks of the at least two vessel regions based on the image data. The method further includes determining an absolute perfusion of the tissue of interest based on the image data. The method further includes computing a standardized perfusion value based on the time difference and the absolute perfusion. The method further includes displaying the standardized perfusion value.

In another aspect, a contrast data processor includes a contrast material level determiner that determines a level of contrast enhancement in at least two vessel regions and at least one tissue of interest from contrast enhanced perfusion image data from a scan of a subject. The contrast data processor further includes a parameter determiner that determines a blood flow time difference between contrast material peaks of the at least two vessel regions based on the image data and an absolute perfusion of the tissue of interest based on the image data. The contrast data processor further includes a metric determiner that computes a standardized perfusion value based on the time difference and the absolute perfusion.

In another aspect, an imaging system includes at least one of a CT, MRI, US, PET, or SPECT scanner and a processing system. The processing system includes a contrast level material determiner that determines a level of enhancement or activity in at least two vessel regions and at least one tissue of interest from perfusion image data from a scan of a subject, a parameter determiner that determines a blood flow time difference between enhancement or activity peaks of the at least two vessel regions based on the image data and an absolute perfusion of the tissue of interest based on the image data, and a metric determiner that computes a standardized perfusion value based on the time difference and the absolute perfusion.

The invention may take form in various components and arrangements of components, and in various steps and arrangements of steps. The drawings are only for purposes of illustrating the preferred embodiments and are not to be construed as limiting the invention.

FIG. 1 schematically illustrates example imaging system in connection with a contrast data processor.

The following describes an approach for determining an accurate and reliable SPV. Perfusion imaging data from CT, MRI, PET, SPECT, US, etc. can be used to determine the data used to compute the SPV. However, for sake of brevity and clarity, the following describes an approach using CT perfusion imaging data.

Figure 1:
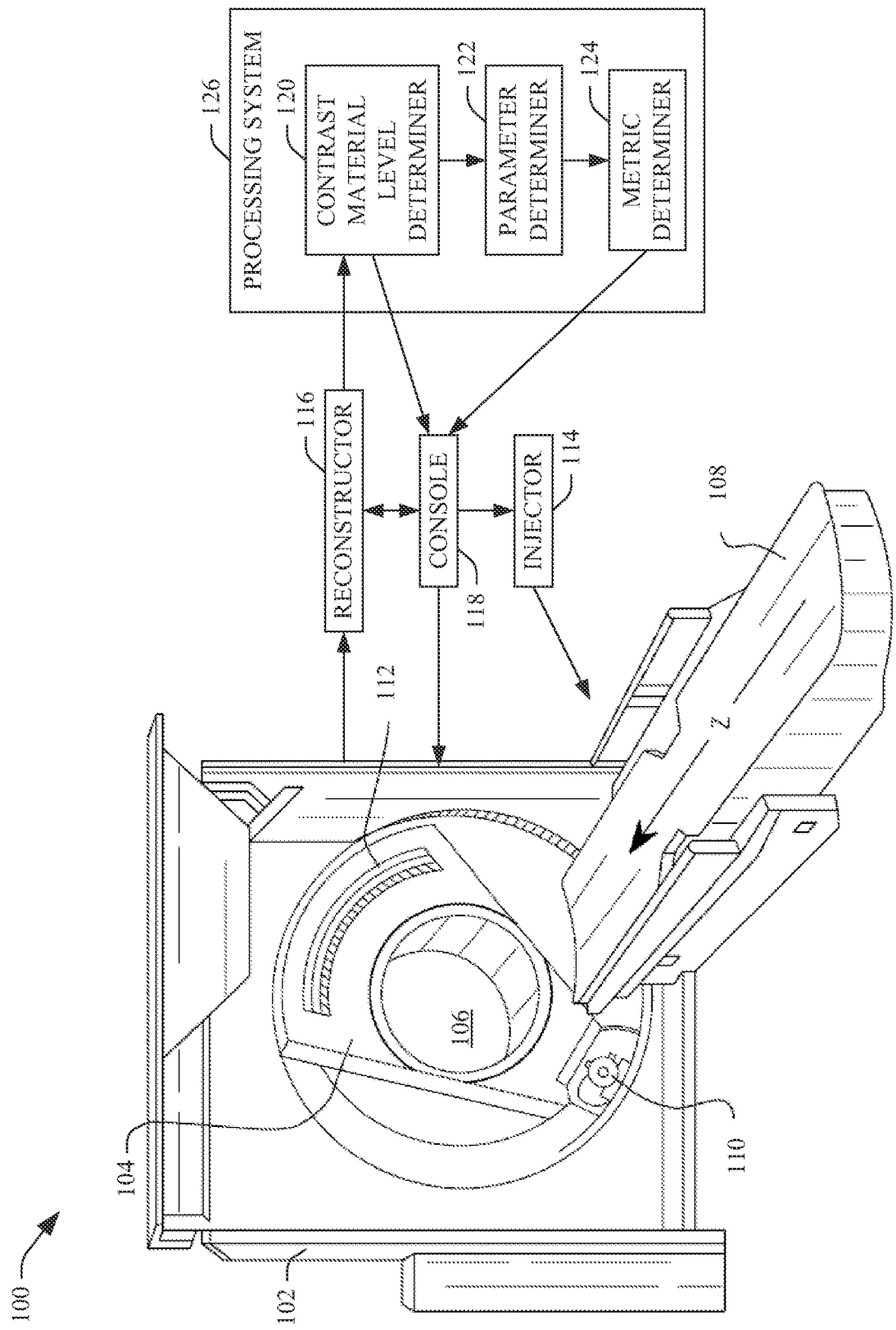

Initially referring to FIG. 1, an imaging system 100 such as a CT scanner is illustrated. The imaging system 100 includes a generally stationary gantry 102 and a rotating gantry 104, which is rotatably supported by the stationary gantry 102 and rotates around an examination region 106 about a z-axis. A subject support 108, such as a couch, supports an object or subject in the examination region 106.

A radiation source 110, such as an x-ray tube, is rotatably supported by the rotating gantry 104, rotates with the rotating gantry 104, and emits polychromatic radiation that traverses the examination region 106. A radiation sensitive detector array 112 subtends an angular arc opposite the radiation source 110 across the examination region 106. The radiation sensitive detector array 112 detects radiation traversing the examination region 106 and generates a signal indicative thereof for each detected photon.

An optional injector 114 is configured to inject a contrast material(s), for example, for a contrast enhanced imaging procedure, such as a perfusion scan. The illustrated injector 114 is controlled by the imaging system 100, which may trigger or invoke in the injector 114 to administer the contrast material. A contrast material(s) can alternatively be manually administered by a clinician or the like. Where the contrast material(s) is manually administered, the injector 114 can be omitted.

A reconstructor 116 reconstructs the projection, generating volumetric image data indicative of a scanned portion of a subject or object located in the imaging region 106. A general-purpose computing system or computer serves as an operator console 118. The console 118 includes a human readable output device such as a monitor and an input device such as a keyboard, mouse, etc. Software resident on the console 118 allows the operator to interact with and/or operate the scanner 100 via a graphical user interface (GUI) or otherwise.

A processing system 126 includes a contrast material level determiner 120, a parameter determiner 122, and/or a metric determiner 124. In another embodiment, the contrast material level determiner 120, the parameter determiner 122, and/or the metric determiner 124 are part of the console 118. In yet another embodiment, the contrast material level determiner 120, the parameter determiner 122, and/or the metric determiner 124 are part of another computing system, which may be local to the system 100 or remote therefrom (e.g., located in another room, distributed across a network, etc.)

The contrast material level determiner 120 determines a level or concentration of contrast material uptake and washout in vessel regions and/or tissue of interest based on the volumetric image data. The parameter determiner 122 determines one or more perfusion parameters based on the level or concentration of the contrast material uptake and washout. The metric determiner 124 determines one or more perfusion metrics based on the determined one or more perfusion parameters. As described in greater detail below, this includes determining a standardized perfusion value (SPV) metric based on a blood flow time difference between blood flow in two different vessel regions and absolute perfusion in tissue of interest.

The contrast material level determiner 120, the parameter determiner 122, and/or the metric determiner 124 can be implemented via one or more processor executing one or more computer readable instructions stored on computer readable storage medium such as physical memory and/or other non-transitory medium. Additionally or alternatively, the contrast material level determiner 120, the parameter determiner 122, and/or the metric determiner 124 can be implemented via one or more processor executing one or more computer readable instructions carried by a carrier wave, a signal and/or other transitory medium.

The following describes the contrast material level determiner 120, the parameter determiner 122, and the metric determiner 124 in greater detail. Generally, for determining the SPV, first and second vessel regions of a subject, one downstream from the other, and a third region (tissue of interest) of the subject, which receives blood from any branch of the body circulatory system, are scanned using a contrast enhanced perfusion protocol. The resulting perfusion image data can be quantified, as shown in FIG. 2, via three different time attenuation curves (TAC's) 202, 204 and 206 for the three different regions.

Figure 2:
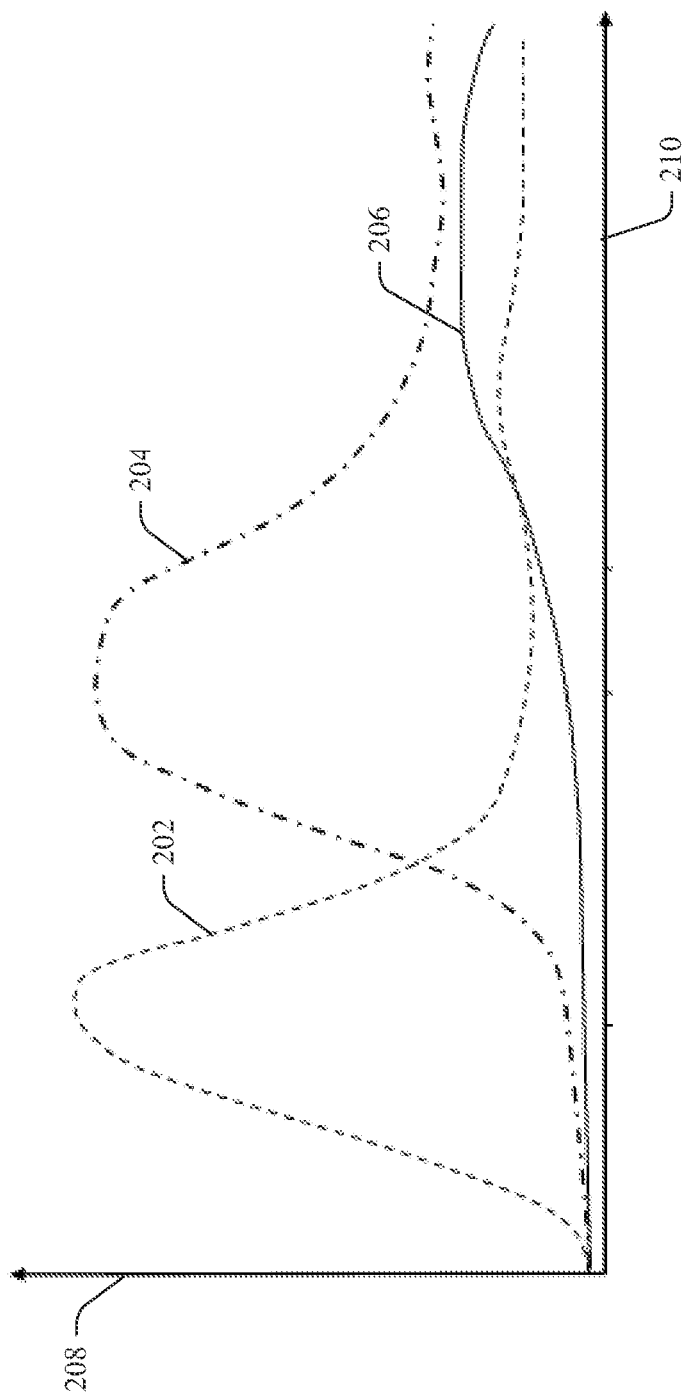
FIG. 2 illustrates example time attenuation curves.

In FIG. 2, an x-axis 210 represents time and a y-axis 208 represents contrast enhancement level. The TAC 202 represents contrast uptake and washout in connection with the first vessel region as a function of time, the TAC 204 represents contrast uptake and washout in connection with the second vessel region as a function of time, and the TAC 206 represents contrast uptake and at least partial washout in connection with a third region or tissue of interest as a function of time.

Figure 3:
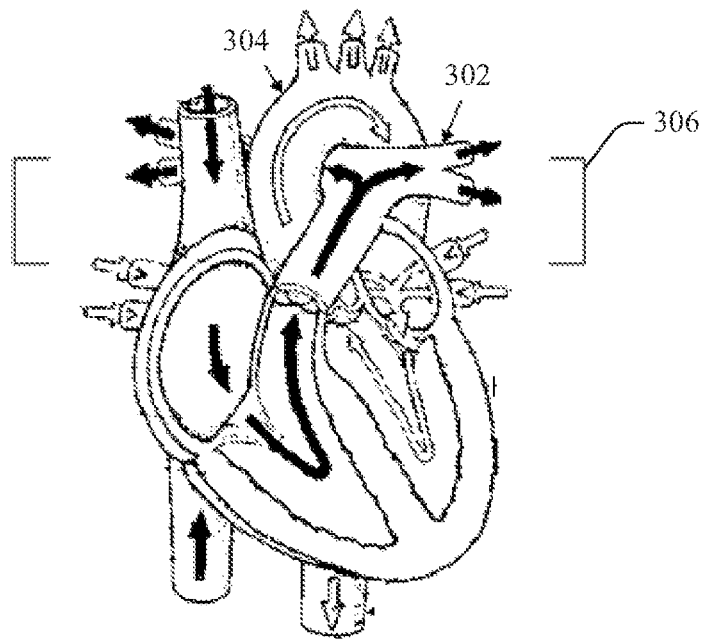
FIG. 3 illustrates example vessels that can be scanned together in a first axial scan window.
Figure 4:
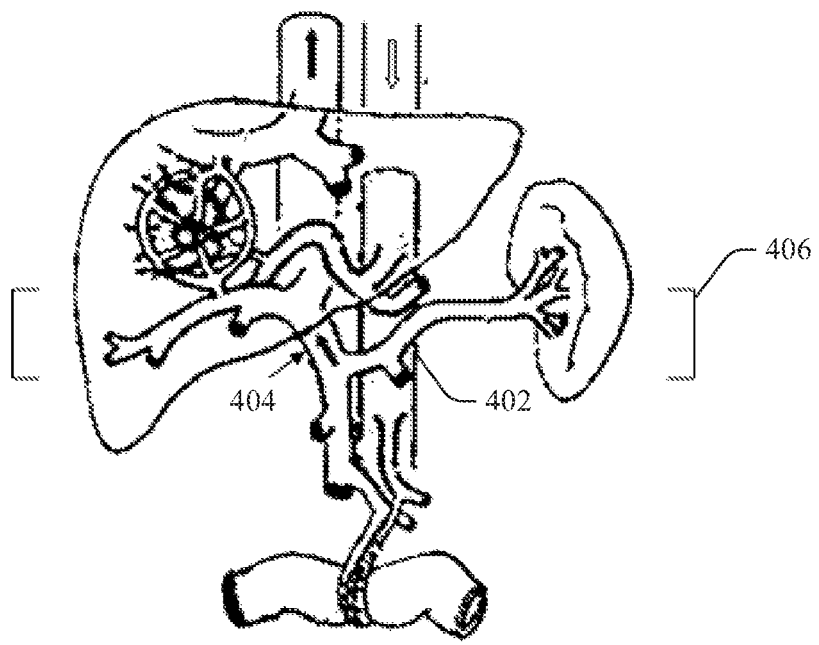
FIG. 4 illustrates example vessels that can be scanned together in a second axial scan window.

In one instance, all three regions are captured in a same scan window. In another instance, two of the three regions of interest are captured in a same scan window, and a third of the three regions is captured in a different scan window. In yet another instance, all three regions are captured in different scan windows. FIG. 3 shows an example of two vessel regions—the pulmonary artery 302 and the aorta 304—that can be captured in a same axial scan window 306. FIG. 4 shows another example of two vessel regions the aorta 402 and the hepatic portal vein 404—that can be captured in a same axial scan window 406.

Figure 5:
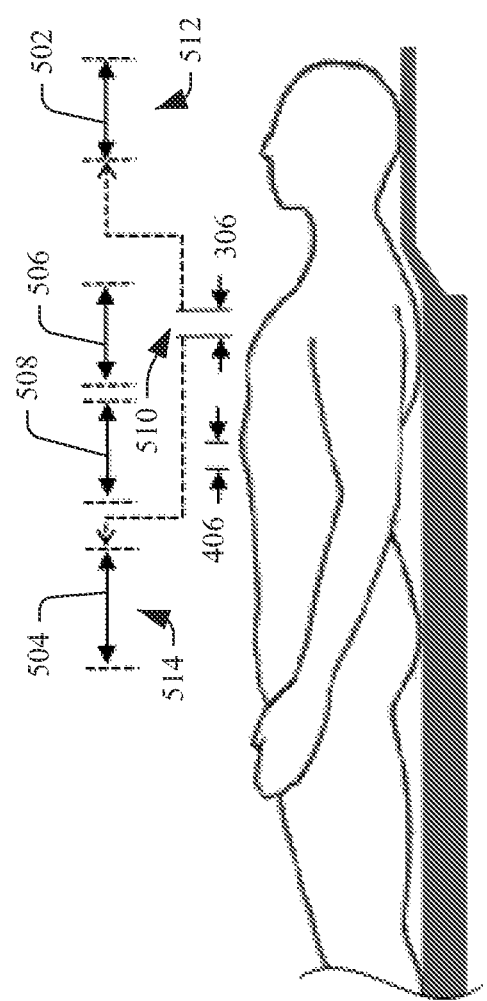
FIG. 5 illustrates example axial scan windows for vessels and for tissue of interest.

FIG. 5 shows the axial scan windows 306 and 406 as well as other axial scan windows 502, 504, 506 and 508, which corresponding to non-limiting examples of tissue of interest for perfusion studies.

In FIG. 5, the axial scan window 502 corresponds to tissue of interest and is spatially separated from the axial scan windows 306 and 406. Likewise, the axial scan window 504 corresponds to tissue of interest and is spatially separated from the axial scan windows 306 and 406.

As such, the pulmonary artery 302 and the aorta 304 (FIG. 3) can be captured in the axial scan window 306 and the head can be captured in the axial scan window 502 (or the kidneys or prostate can be captured in the axial scan window 504). Alternatively, the aorta 402 and the hepatic portal vein 404 (FIG. 3) can be captured in the scan window 406 and the kidneys or prostate can be captured in the axial scan window 504 (or the head can be captured in the axial scan window 502).

The axial scan window 506 corresponds to tissue of interest and overlaps the axial scan window 306 and is spatially separated from the axial scan window 406, and the axial scan window 508 corresponds to tissue of interest and overlaps the axial scan window 406 and is spatially separated from the axial scan window 306.

As such, the pulmonary artery 302, the aorta 304, and the lungs can all be captured in the axial scan window 506, the aorta 402, the portal vein 404, and the liver or pancreases can all be captured in the axial scan window 508. In these instances, the subject support 108 (FIG. 1) remains at the same location, or jogging back and forth to cover the axial region, although different scan extents may be used, depending on whether the first and second vessels regions or the tissue of interest is being scanned.

Alternatively, the pulmonary artery 302 and the aorta 304 can be captured in the axial scan window 306 and the lungs can be captured in the axial scan window 506, or the aorta 402 and the hepatic portal vein 404 can both be captured in the axial scan window 406 and the liver, prostate, kidney, pancreases, etc. can be capture in the axial scan window 504. In these instances, the subject support 108 (FIG. 1) moves the subject between axial scan windows.

In the latter instance, for example, the subject support 108 positions the subject to correspond to a scan position 510 for scanning the first and second vessels and the first and second vessels are scanned until a certain time point is reached. Then, the subject support 108 positions the subject to correspond to a second scan position 512 or 514, which does not overlap the first position, for scanning the tissue of interest and the tissue of interest is scanned until another time point is reached.

The above examples of vessel regions and/or tissue of interest are not limiting. For example, the vessel regions can be the pulmonary artery and the aorta region near the heart, the aorta and the hepatic portal vein near the liver, the primary and the recirculated peaks in one of the pulmonary artery or the aorta, the aorta and the superior vena cava, the aorta and the inferior vena cava, the carotids arteries and the adjacent veins in the neck region, and/or other reference pairs of blood vessel regions.

Figure 6:
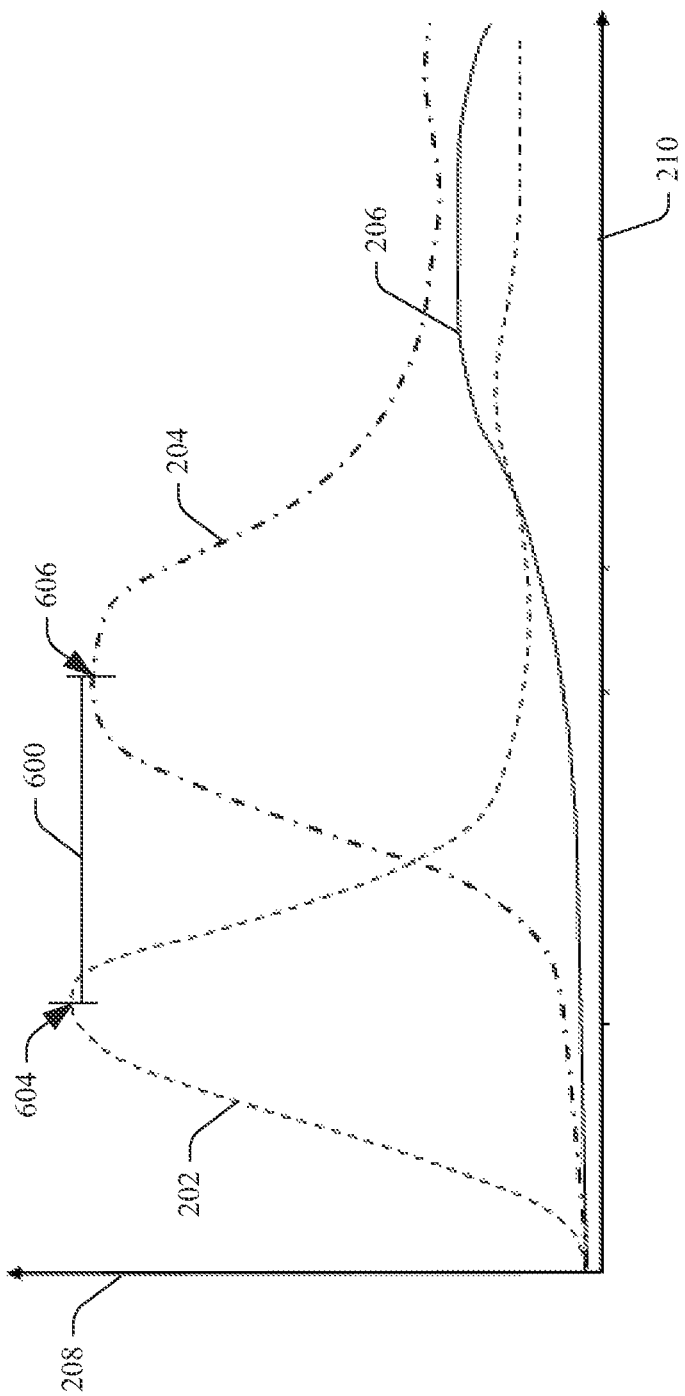
FIG. 6 illustrates an example for determining a time difference between contrast material peaks in different time attenuation curves.

The parameter determiner 122 determines one or more perfusion parameters based on the TAC's 202-206. For example, the parameter determiner 122 can determine a time from contrast administration to peak contrast enhancement (e.g., time to peak (TTP)) for one or more of the TAC's 202-206. The parameter determiner 122 can also determines a time difference based on two of the TAC's 202-206. The time difference can be between mean transit times (i.e. "center of gravity" or the 'first momentum') of two TAC's, or the difference between the two time points representing maximal gradients occurrences. Optionally, Gamma-variate models can be fit to the TAC's. FIG. 6 shows an example of determining a time difference 600 between peaks 604 and 606 of the TAC's 202 and 204.

Figure 7:
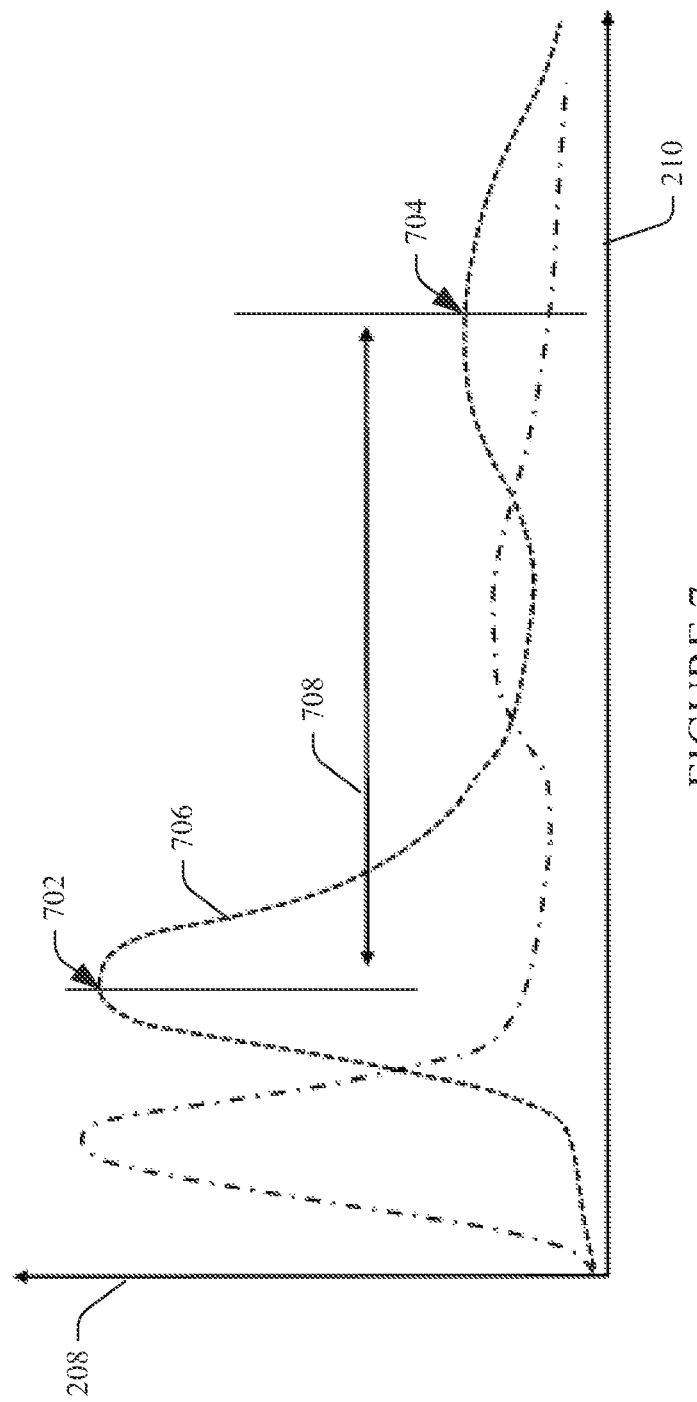
FIG. 7 illustrates an example for determining absolute perfusion for the tissue of interest.

The parameter determiner 122 can also determine a total body perfusion parameter from a first peak 702 and a re-circulation peak 704 of a TAC 706 by computing the inverse of the time difference 708 therebetween, which is shown in FIG. 7. The total body perfusion value, generally, is the rate at which the total body blood volume circulates one turn in the circulatory system. In principle it can be calculated if the first pass and the second pass (the recirculation) curves can be measured.

Another option for determining a total body perfusion includes finding a general model which correlates the true total body perfusion to the measured time difference. There is a reasonable chance that the correlation will be expressed as a constant multiplication factor for all patients (at least in a good approximation), since for example the ratio between the pulmonary system blood-volume to the whole body blood-volume may be almost independent on body weight, age, gender etc.

Another option for determining a total body perfusion is to perform, for each patient, a dedicated calibration measurement. The calibration can be done, for example, before starting a therapy treatment which is planned to be followed-up using perfusion imaging. During the calibration procedure, both the total body perfusion and the planned time difference technique of the diagnostic perfusion protocol will be measured. By calculating the correlation between the total body perfusion to the time difference measured in the perfusion protocol, an individual look-up table (or even a simple factor) can be derived for each patient. The calibration can be done in several different cardiac output rates in order to achieve higher accuracy.

The metric determiner 124 determines one or more perfusion metrics based on the determined one or more perfusion parameters. By way of non-limiting example, in one instance the metric determiner 124 determines a standardized perfusion value (SPV) based on EQUATION 1:

$$SPV = P \times D, \quad \text{EQUATION 1:}$$

where P represents absolute perfusion (e.g., the measured tissue perfusion in specific conditions, etc.) and D represents a flow time difference between reference blood flow regions (e.g., the difference 600, the difference 708, etc.)

Assuming that the heart rate of one patient is higher in a follow-up examination and the absolute perfusion becomes higher only because of the higher heart rate and not because of any change in the examined tissue (even after the common normalization with the aorta curve), the measured time difference D in this case will be smaller due to the faster blood flow. Thus, the standardized perfusion value will probably not change relative to an earlier perfusion study as it should be since nothing had changed in the examined tissue.

Another non-limiting example metric is shown in EQUATION 2:

$$SPV = P \times F(D),\qquad \text{EQUATION 2:}$$

where F is a model function or a look up table derived from a priori information or a pre-calibration, which compares the measured time difference with another method that determines the total body perfusion.

The computed SPV can be visually presented via a monitor in a manner similar to the way conventional perfusion maps are presented. In addition, analysis graph and/or numeric results, such as the information shown in FIGS. 2, 6 and 7 can be visually presented.

Variations are contemplated next.

As an option, one or more pre-scans without injecting the contrast material, or test bolus scans with contrast material taken before the perfusion imaging, can help to achieve higher accuracy. In one instance, the flow time difference itself, determined from the first and second vessel regions, may be obtained by a test bolus perfusion scan before or after the diagnostic perfusion scan of the examined range.

In another instance, if the injected contrast material bolus of the perfusion scan is short in time, the tissue perfusion may be calculated accurately even without measuring the beginning part of the TAC. In such cases, there is sufficient time to measure the first and second vessel regions and only then to move to the examined area. If the planned contrast injection is not short enough it is possible to use a pre-scan (without contrast material) for measuring the baseline tissue enhancement.

In another instance, the planned time point for moving from the first and second vessel regions to the tissue of interest may be determined, prior to the diagnostic perfusion scan, by a test bolus scan which enables to estimate the relevant time constants of the specific patient blood circulation.

Figure 8:
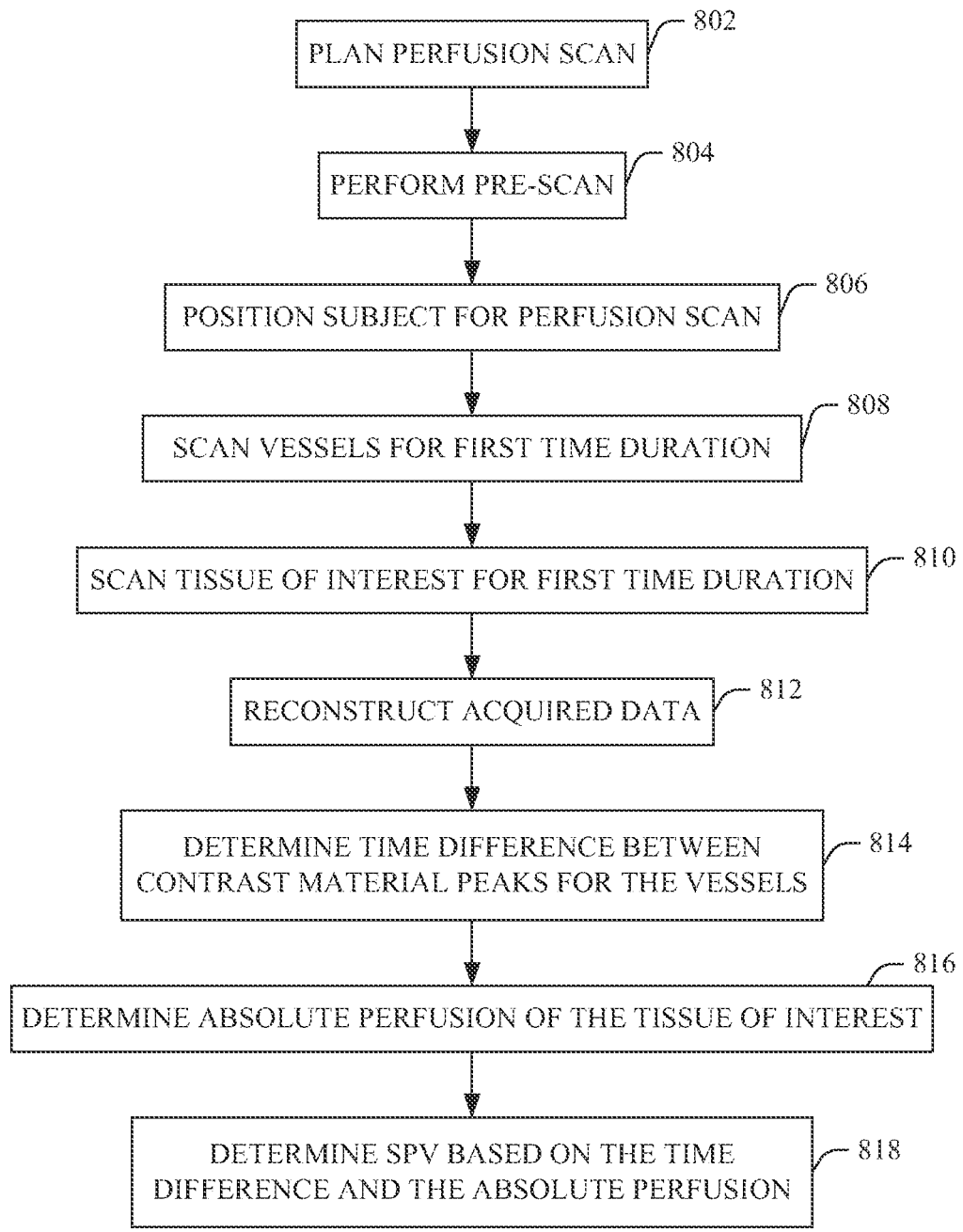
FIG. 8 illustrates a method of determining a SPV where an axial scan window for the vessel regions and the tissue of interest overlap.

FIG. 8 illustrates a method of determining a SPV based on a contrast enhanced perfusion scan in which the axial scan window for the vessel regions and the tissue of interest overlap.

It is to be appreciated that the ordering of the acts is not limiting. As such, other orderings are contemplated herein. In addition, one or more acts may be omitted and/or one or more additional acts may be included.

At 802, a perfusion scan is planned. This includes planning one or more scans of two different vessel regions, one downstream from the other, and a scan of the tissue of interest.

At 804, optionally, a non-contrast pre-scan is performed. The non-contrast pre-scan is optional depending on the perfusion calculation method. For example, if maximum slope model is used, the pre-scan may be omitted.

At 806, the subject support positions a subject for the perfusion scan.

At 808, a first part of the perfusion scan is performed based on the plan, including scanning the axial scan window corresponding to the vessel regions for a first time duration.

At 810, a second part of the perfusion scan is performed based on the plan, including scanning the axial scan window corresponding to the tissue of interest for a second time duration.

At 812, the data acquired for the first and second parts of the perfusion scan is reconstructed.

At 814, a time difference between contrast material flow peaks is determined for the vessels from the image data.

At 816, an absolute perfusion is determined for the tissue of interest based on contrast material flow from the image data.

At 818, a SPV is calculated based on the difference and the absolute perfusion, for example, as described herein using EQUATIONS 1 or 2, and/or otherwise.

Figure 9:
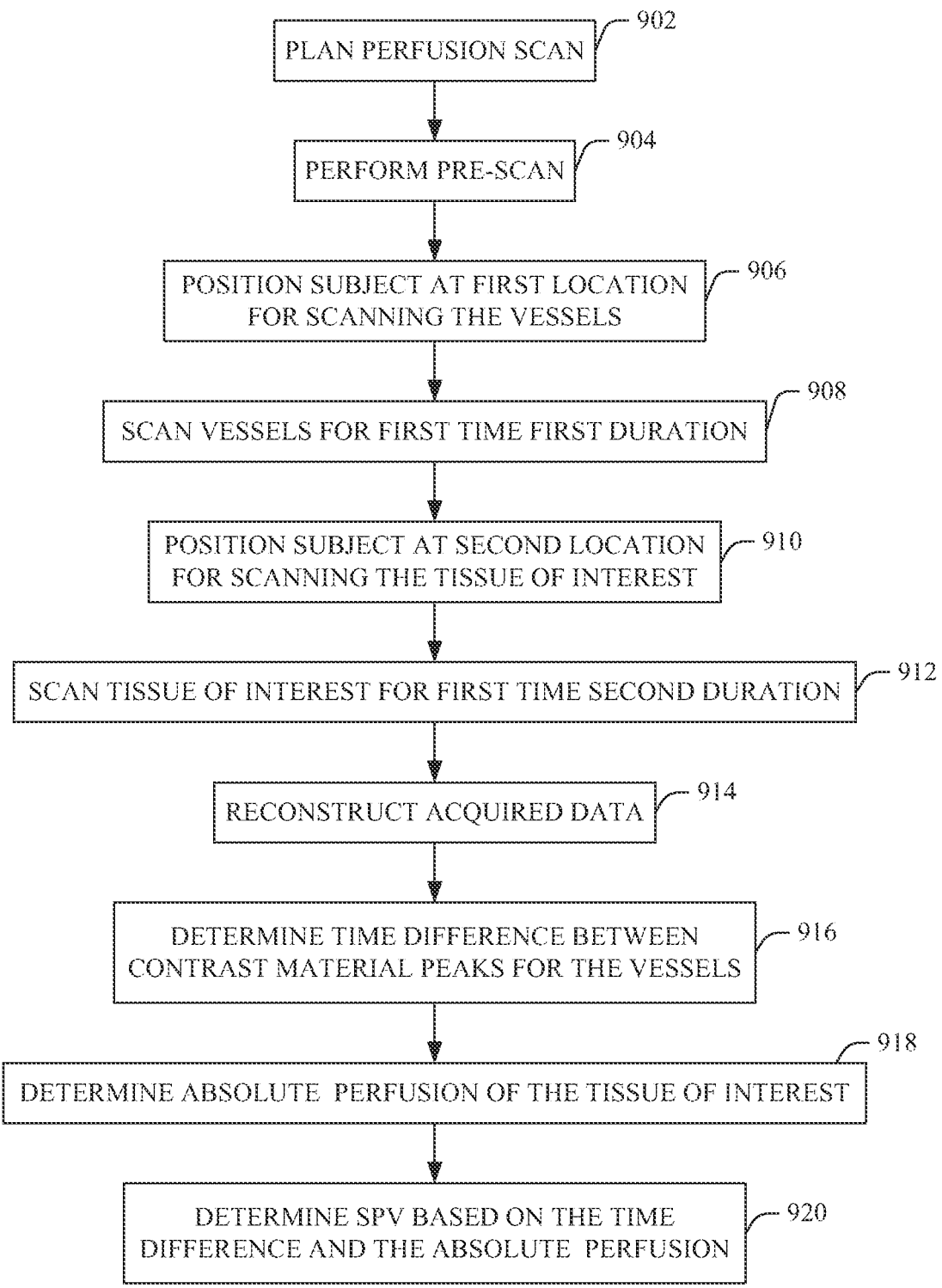
FIG. 9 illustrates a method of determining a SPV where an axial scan window for the vessel regions and the tissue of interest do not overlap.

FIG. 9 illustrates a method of determining a SPV based on a contrast enhanced perfusion scan in which the axial scan window for the vessel regions and the tissue of interest do not overlap.

It is to be appreciated that the ordering of the acts is not limiting. As such, other orderings are contemplated herein. In addition, one or more acts may be omitted and/or one or more additional acts may be included.

At 902, a perfusion scan is planned. This includes planning one or more scans of two different vessel regions, one downstream from the other, and a scan of the tissue of interest.

At 904, optionally, a non-contrast pre-scan is performed, as described in act 804 of FIG. 8.

At 906, the subject support positions a subject at a first location corresponding to the axial scan range of the vessel regions.

At 908, a first part of the perfusion scan is performed based on the plan, including scanning the axial scan range of the vessel regions for a first time duration.

At 910, after the first duration, the subject support positions the subject at a second different location corresponding to the axial scan range of the tissue of interest.

At 912, a second part of the perfusion scan is performed based on the plan, including scanning the axial scan range of the tissue of interest for a second time duration.

At 914, the data acquired for the first and second parts of the perfusion scan is reconstructed.

At 916, a difference between the time to contrast material peaks is determined.

At 918, an absolute perfusion is determined for the region of interest base on the corresponding image data.

At 920, a SPV is calculated based on the difference and the absolute perfusion, for example, as described herein using EQUATIONS 1 or 2, and/or otherwise.

Figure 10:
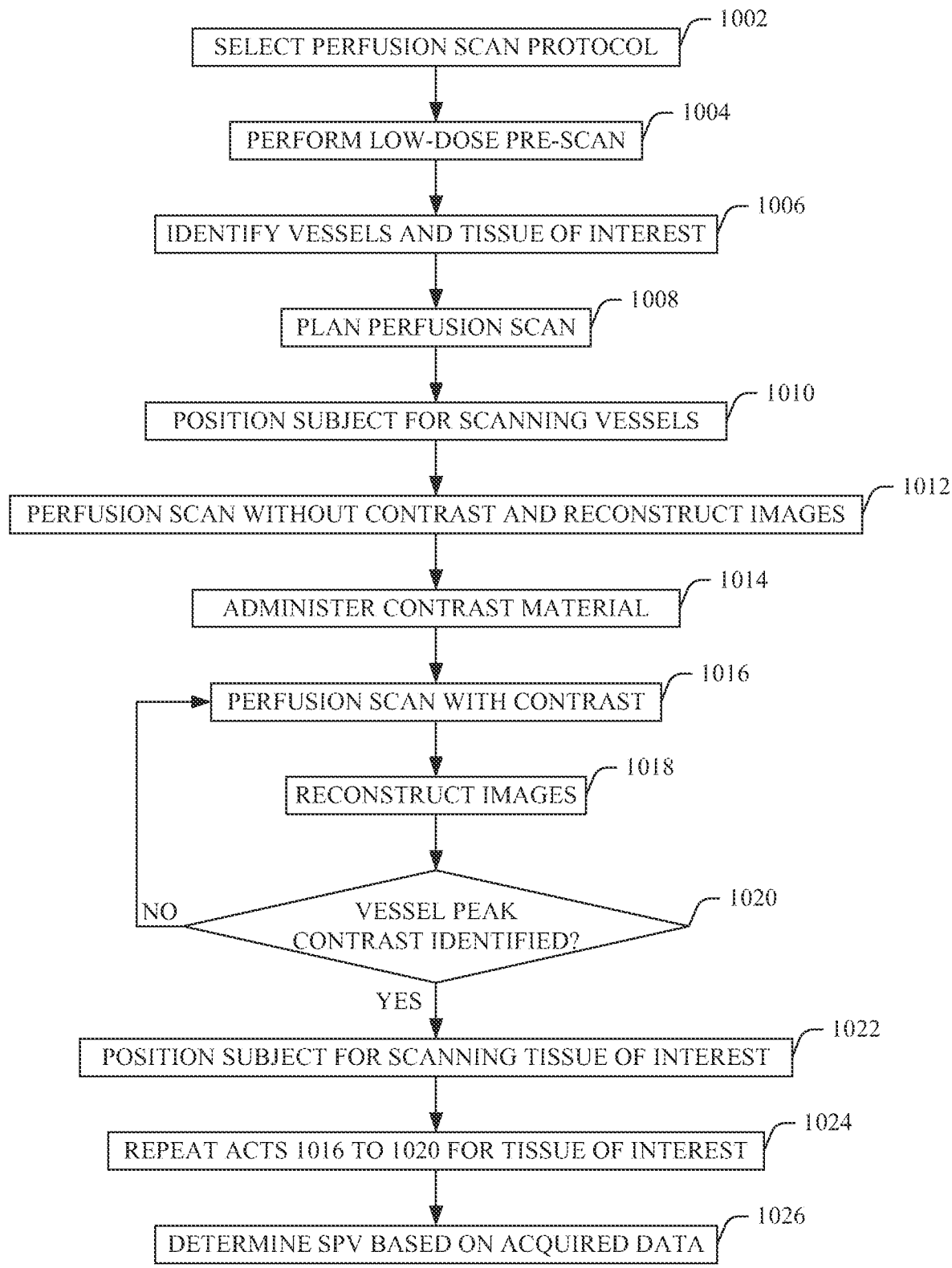
FIG. 10 illustrates a method of determining a SPV where an axial scan window for the vessel regions and the tissue of interest do not overlap using real time image data to position the subject.

FIG. 10 illustrates a method of determining a SPV based on a contrast enhanced perfusion scan in which the axial scan window for the vessel regions and the tissue of interest do not overlap using real time image data to position the subject.

It is to be appreciated that the ordering of the acts is not limiting. As such, other orderings are contemplated herein. In addition, one or more acts may be omitted and/or one or more additional acts may be included.

At 1002, a perfusion scan protocol is selected.

At 1004, a low-dose pre-scan is performed.

At 1006, reference vessel regions are identified from the pre-scan.

At 1008, a perfusion scan plan is created, identifying vessel regions and tissue of interest to scan.

At 1010, the subject is positioned for scanning the vessels.

At 1012, the perfusion scan begins to be performed without any contrast and images are reconstructed in real time.

At 1014, contrast is administered to the subject.

At 1016, the perfusion scan is performed with contrast.

At 1018, images are reconstructed in real time.

At 1020, the acquired data is analyzed to determine if peak contrast enhancement in the vessels has been reached.

If peak contrast enhancement has not been reached, then acts 1016-1020 are repeated.

If peak contrast enhancement has been reached, then at 1022 the subject is moved to a second different position for scanning the tissue of interest.

At 1024, acts 1016-1020 are repeated for the tissue of interest.

At 1026, a SPV is calculated based on the acquired data, for example, as described herein using EQUATIONS 1 or 2, and/or otherwise.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

Although the above is described in connection with CT, imaging data from contrast perfusion scans performed with MRI, PET, SPECT, etc. imaging systems can also be used to generate data used to compute the SPV. Examples of such scans include MRI with gadolinium or iron-oxide contrast agent, PET and SPECT with several types of radiotracers, and ultrasound with micro-bubbles contrast agents. In animal preclinical imaging, optical tomography with fluorescent agents is applicable as well.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
   obtaining contrast enhanced perfusion imaging data of at least two vessel regions, one vessel region of the at least two vessel regions being downstream from another vessel region of the at least two vessel regions with respect to contrast agent flow, and at least one tissue of interest, which receives blood from the circulatory system, of a scanned subject;
   determining a blood flow time difference between contrast material peaks of the at least two vessel regions based on the image data, the determining of the blood flow time difference including determining a time delay of contrast agent peaks, in the one vessel region and the other vessel region, of a common contrast agent that flows from the other vessel region to the one vessel region;
   determining an absolute perfusion of the tissue of interest as a function of a measured perfusion parameter of the contrast agent flow, wherein the measured perfusion parameter is determined from the image data;
   computing a standardized perfusion value as a function of the absolute perfusion and the time difference; and
   displaying the standardized perfusion value.

2. The method of claim 1, further comprising:
   generating a first contrast flow behavior for a first of the at least two vessel regions;
   determining a first time to the peak contrast enhancement for the first of the at least two vessel regions based on the first behavior;
   generating a second contrast flow behavior for a second of the at least two vessel regions;
   determining a second time to the peak contrast enhancement for the second of the at least two vessel regions based on the second behavior;
   determining the time difference based on the first time to the peak contrast enhancement and second time to the peak contrast enhancement.

3. The method of claim 2, further comprising:
   determining the time difference based on a mean transit time value of the first contrast enhancement and a mean transit time value of the second contrast enhancement.

4. The method of claim 2, further comprising:
   determining the time difference based on a maximal gradient occurrence of the first contrast enhancement and a maximal gradient occurrence of the second contrast enhancement.

5. The method of claim 1, further comprising:
   generating a contrast flow behavior for the tissue of interest;
   determining a first peak based on the behavior;
   determining a maximal gradient based on the behavior;
   determining area under the curve and peak enhancement of at least one of the two vessel regions; and
   computing the absolute tissue perfusion based on the determined parameters.

6. The method of claim 1, further comprising:
   computing the standardized perfusion value as a product of the absolute perfusion and the time difference.

7. The method of claim 1, further comprising:
   computing the standardized perfusion value as a product of the absolute perfusion and a function of the time difference.

8. The method of claim 7, wherein the function compares the computed time difference between the peaks with at least one of a pre-determined total body perfusion or a normalizing blood flow indicator.

9. The method of claim 1, further comprising:
   acquiring contrast enhanced perfusion imaging data corresponding to the at least two vessel regions within a same axial scan window.

10. The method of claim 9, further comprising:
    acquiring contrast enhanced perfusion imaging data corresponding to the tissue of interest within the same axial scan window.

11. The method of claim 9, further comprising:
    acquiring contrast enhanced perfusion imaging data corresponding to the tissue of interest within different axial scan windows.

12. The method of claim 11, further comprising:
    moving the subject between a first location at which the contrast enhanced perfusion imaging data corresponding to the tissue of interest is acquired and a second different location at which the contrast enhanced perfusion imaging data corresponding to the tissue of interest is acquired.

13. The method of claim 12, further comprising:
    moving the subject from the first location and the second location after a predetermined period of time lapses.

14. The method of claim 12, further comprising:
    moving the subject from the first location to the second location based on real time reconstructed images which visually indicate when contrast enhancement peaks in the at least two vessel regions.

15. The method of claim 1, wherein the contrast material peaks comprise a first peak and a recirculation peak and wherein the absolute perfusion is further determined as a function of an inverse time difference between the first peak and recirculation peak.

16. The method of claim 1, wherein the function that computes the standardized perfusion value is SPV=P×D, wherein SPV is the standardized perfusion value, P is the absolute perfusion value, and D is the time difference.

17. The method of claim 1, wherein the function that computes the standardized perfusion value is SPV=P×F(D), wherein P is the absolute perfusion value, D is the time difference, and F is a model function or a look up table derived from a priori information or a pre-calibration.

18. A processing system, comprising:
a processor, wherein the processor:
determines a level of contrast enhancement in at least two vessel regions and at least one tissue of interest from contrast enhanced perfusion image data from a scan of a subject, one vessel region of the at least two vessel regions being downstream from another vessel region of the at least two vessel regions with respect to contrast agent flow;
determines a blood flow time difference between contrast material peaks of the at least two vessel regions based on the image data and an absolute perfusion of the tissue of interest, wherein the absolute perfusion is a function of a measured perfusion parameter of a contrast agent flow and wherein the measured perfusion parameter is determined from the image data, the determining of the blood flow time difference including determining a time delay of contrast agent peaks, in the one vessel region and the other vessel region, of a common contrast agent that flows from the other vessel region to the one vessel region; and
computes a standardized perfusion value as a function of the time difference and the absolute perfusion.

19. The processing system of claim 18, wherein the processor computes the standardized perfusion value as a product of the absolute perfusion and the time difference.

20. The processing system of claim 18, wherein the processor computes the standardized perfusion value as a product of the absolute perfusion and a function of the time difference.

21. The processing system of claim 20, wherein the function compares the computed time difference between the peaks with at least one of a pre-determined total body perfusion or a normalizing blood flow indicator.

\* \* \* \* \*